United States Patent [19]
Takahashi et al.

[11] Patent Number: 5,846,793
[45] Date of Patent: Dec. 8, 1998

[54] MICROBIAL PROCESS FOR BIOTRANSFORMATION TO (R)-3-CHLORO-1,2-PROPANEDIOL

[75] Inventors: Hideyuki Takahashi, Kakogawa; Satoru Tsuda; Yoshio Nakamura, both of Takasago; Masahiro Ogura, Ono; Tadayoshi Shiraishi, Takasago; Yoshio Shimada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 632,663

[22] Filed: Dec. 27, 1990

Related U.S. Application Data

[63] Continuation of Ser. No. 177,755, Apr. 5, 1988, abandoned.

[30] Foreign Application Priority Data

Apr. 7, 1987 [JP] Japan ..................... 62-85248

[51] Int. Cl.$^6$ ..................................... C12P 7/18
[52] U.S. Cl. ..................... 435/158; 435/157; 435/252.1; 435/244
[58] Field of Search ..................... 435/158, 157, 435/252.1, 244

[56] References Cited

U.S. PATENT DOCUMENTS

| | | | |
|---|---|---|---|
| 4,313,008 | 1/1982 | Jones | 568/844 |
| 5,017,484 | 5/1991 | Nakamura | 435/158 |

FOREIGN PATENT DOCUMENTS

| | | |
|---|---|---|
| 0 060 595 | 9/1982 | European Pat. Off. . |
| 8 504 900 | 11/1985 | WIPO . |

OTHER PUBLICATIONS

Hohn–Bentz et al., *Arch. Microbiol.* 116, pp. 197–203, 1978
Sigma Catalog, 1987, pp. 184–185.
J. Bacteriology 140, No. 1, 182–187 (1979), C.T. Tang et al.
J. Org. Chem. 50, No. 1, 1992–1994 (1985), Chi–huey Wong et al.
J. Biol. Chem. 249, No. 10, 3132–3139 (1974), W.G. McGregor et al.
Chemistry and Industry, "Stereospecific Synthesis of R– and S–3–chloropropan–1,2–diol", Jul. 15, 1978.
Patent Abstracts of Japan, vol. 11, no. 267 (C–443)[2714], 28th Aug. 1987; & JP–A–62 993 (Osaka Soda Co., Ltd. ) 31 Mar. 1987.
ATCC Catalogue of Bacteria, 1992, p. 286.

*Primary Examiner*—Irene Marx
*Attorney, Agent, or Firm*—Armstrong, Westerman, Hattori, McLeland & Naughton

[57] ABSTRACT

A process for preparing optically active (R)-3-chloro-1,2-propanediol, which comprises subjecting (R,S)-3-chloro-1,2-propanediol to the reaction of a microorganism belonging to genus Serratia in a reaction mixture, and then collecting the residual (R)-3-chloro-1,2-propanediol. According to the process of the present invention, (R)-3-chloro-1,2-propanediol can be efficiently prepared starting from low cost (R,S)-3-chloro-1,2-propanediol.

1 Claim, No Drawings

MICROBIAL PROCESS FOR BIOTRANSFORMATION TO (R)-3-CHLORO-1,2-PROPANEDIOL

This application is a continuation of application Ser. No. 177,755 filed Apr. 5, 1988 now abandoned.

BACKGROUND OF THE INVENTION

The present invention relates to a process for preparing optically active (R)-3-chloro-1,2-propanediol.

The optically active (R)-3-chloro-1,2-propanediol is a useful starting material for synthesizing a variety of drugs and optically active compounds having physiological activity. For example, (R)-3-chloro-1,2-propanediol has been used for synthesizing L-carnitine (Japanese Unexamined Patent Publication No. 165352/1982).

As a process for preparing (R)-3-chloro-1,2-propanediol, a method employing methyl-5-chloro-5-deoxy-a-L-arabinofuranoside [Hayden F. Jones, Chemistry and Industry, p 533, 15 Jul., 1978], a method employing 1,2,5,6-diacetonyl-D-mannitol [H. Jackson et al., Chem. Biol. Interactions, 13, p 193 (1976); Y. Kawakami et al., Journal of Organic Chemistry, 47, p 3581 (1982)] or the like is known.

However, the above processes are not suitable for industrial production due to disadvantages such as difficulty in obtaining the expensive starting material and complicated steps. Therefore, an industrially advantageous process has been earnestly desired for preparing the (R)-3-chloro-1,2-propanediol.

It was found that (R)-3-chloro-1,2-propanediol can be easily prepared by subjecting low-priced (R,S)-3-chloro-1,2-propanediol to the action of a microorganism, and thereby the (S)-3-chloro-1,2-propanediol is selectively metabolized and the (R)-3-chloro-1,2-propanediol remains (Japanese Unexamined Patent Publications No. 122597/1987 and No. 158494/1987). And it was also found that the reaction rate can be accelerated by adding a compound having SH group to the reaction mixture (Japanese Unexamined Patent Publication No. 36798/1988). The substrate concentration in the above process, however, is not high enough, and an efficient process for the preparation by a microorganism having higher activity has been desired to be developed.

SUMMARY OF THE INVENTION

It has been now found that by employing a microorganism belonging to genus Serratia, the charged substrate concentration can be drastically increased (comparing with Japanese Unexamined Patent Publications No. 122597/1987 and No. 158494/1987), furthermore the productivity is raised by adding a compound having SH group to the mixture, and thus the present invention has been accomplished.

According to the present invention, there is provided a process for preparing optically active (R)-3-chloro-1,2-propanediol, which comprises subjecting (R,S)-3-chloro-1,2-propanediol to the action of a microorganism belonging to genus Serratia in a reaction mixture, and then collecting the residual (R)-3-chloro-1,2-propanediol.

DETAILED DESCRIPTION

Examples of the microorganism capable of being employed in the present invention are, for instance, *Serratia marcescens*, *Serratia liquefaciens*, *Serratia marinorubra*, and the like. More particularly, *Serratia marcescens* IFO 12648, IFO 3759, IFO 3736, IFO 3735, IFO 3052, IFO 3046, *Serratia liquefaciens* IFO 12979, *Serratia marinorubra* IFO 12973 are exemplified.

Examples of the compound having SH group, which can be used in the present invention are, for instance, dithiothreitol, dithioerythritol, glutathione, cysteine, mercaptoethanol, thioglycerol, 2,3-dimercaptopropanol, thioacetic acid, dimercaptosuccinic acid, 2-mercaptopropionic acid, 3-mercaptopropionic acid, thioglycollic acid, tert-butyl mercaptan, sodium hydrosulfide, potassium hydrosulfide, and the like.

As the culture medium for culturing the above-mentioned microorganisms, any culture medium where these microorganisms can usually grow can be employed. The culture medium may optionally contain nutrient sources which are employed in the usual culture, for example, sugars such as glucose, sucrose and maltose, alcohols such as ethanol, glycerol and 1,2-propanediol, organic acids such as acetic acid and lactic acid, or the mixture thereof as a carbon source, ammonium sulfate, ammonium phosphate, urea, yeast extract, meat extract or peptone as a nitrogen source, an inorganic salt, trace amounts of metal salt, vitamins and the like.

The microorganisms as mentioned above may be cultured in the conventional manner. For example, the microoganisms are preferably cultured in a culture medium of pH ranging from 4.0 to 9.5 at a temperature of from 20° to 45° C. for 10 to 96 hours under the aerobic condition.

(R,S)-3-chloro-1,2-propanediol is subjected to the action of the microorganism to prepare (R)-3-chloro-1,2-propanediol, for instance, by adding the substrate to a culture solution cultured as mentioned above or to a suspension of the cells obtained by a centrifugation from the above culture solution, by adding the substrate to the culture medium to conduct the culture and the reaction concurrently, or by adding the substrate to a suspension of the immobilized microorganism in a suitable buffer.

The reaction is preferably carried out at a temperature of from 15° to 50° C. at a pH of from 4.0 to 8.0. For obtaining a constant pH value, a suitable buffer and the like can be employed.

The substrate concentration in the reaction mixture is preferably 0.1 to 10 w/v %. The substrate may be added to the reaction mixture either at a stretch or in portions.

When the reaction is conducted, the reaction rate can be accelerated by adding the compound having SH group to the reaction mixture. A concentration of the compound having SH group in the reaction mixture is preferably 0.05 to 10 w/v %. The compound may be added to the reaction mixture either at a stretch together with the substrate or in portions.

The reaction is usually carried out with shaking or stirring. Although the reaction time may vary depending on the reaction condition such as the substrate concentration or the amount of the enzyme, the reaction condition is preferably selected so that the reaction is completed within 72 hours.

In the progress of the reaction, the residual substrate is monitored with a gas chromatography or the like, and then the reaction is preferably stopped when around 50% of the substrate is consumed for obtaining a high yield.

The thus prepared (R)-3-chloro-1,2-propanediol can be collected from the reaction mixture by means of the method usually employed for the collection of optically inactive 3-chloro-1,2-propanediol. For example, after removing the cells from the reaction mixture by a centrifugation and the like, the supernatant is suitably concentrated and the concentrate is extracted with a solvent such as ethyl acetate.

After dehydrating the extract with anhydrous sodium sulfate and the like, the solvent is removed under reduced pressure to give a syrup of (R)-3-chloro-1,2-propanediol, which may be further purified by distillation.

In addition to (R)-3-chloro-1,2-propanediol, (R)-3-bromo-1,2-propanediol and (R)-3-fluoro-1,2-propanediol can be prepared from (R,S)-3-bromo-1,2-propanediol and (R,S)-3-fluoro-1,2-propanediol respectively, in the same manner as in the present invention.

The present invention is described and explained in more detail by means of the following Examples. However, it should be understood that the present invention is not limited to such Examples and various changes and modifications can be made without departing from the scope of the present invention.

EXAMPLES 1 to 3

A culture medium containing 4% of glycerol, 1.3% of $(NH_4)_2HPO_4$, 0.7% of $KH_2PO_4$, 800 ppm of $MgSO_4 \cdot 7H_2O$, 60 ppm of $ZnSO_4 \cdot 7H_2O$, 90 ppm of $FeSO_4 \cdot 7H_2O$, 5 ppm of $CuSO_4 \cdot 5H_2O$, 10 ppm of $MnSO_4 \cdot 4H_2O$, 100 ppm of NaCl and 0.3% of yeast extract was prepared with deionized water (pH 7.0). Each 500 ml Sakaguchi flask charged with 50 ml of the culture medium was sterilized at 120° C. for 20 minutes.

Each microorganism shown in Table 1 was inoculated into the above culture medium and the shaking culture was conducted at 30° C. for 48 hours. The cells were collected by the centrifugation of 300 ml of the culture solution and were washed with water. To a suspension of the cells in 200 ml of 0.3M phosphate buffer (pH 7.0) was added 4 g of (R,S)-3-chloro-1,2-propanediol to conduct the reaction at 30° C. for 48 hours with shaking.

After removing the cells from 100 ml of the reaction mixture by the centrifugation, the supernatant was concentrated to about 10 ml and was extracted three times with 20 ml of ethyl acetate (total 60 ml). The extract was dehydrated with anhydrous sodium sulfate and then the solvent was removed under reduced pressure to give a syrup.

Specific rotatory power of the syrup was measured to give the values as shown in Table 1.

TABLE 1

| Example No. | Strain | Yield* (%) | Specific rotatory power $[\alpha]_D^{20}$ (C = 2, $H_2O$) |
|---|---|---|---|
| 1 | Serratia marcescens IFO 12648 | 32 | −7.38 |
| 2 | Serratia liquefaciens IFO 12979 | 23 | −8.45 |
| 3 | Serratia marinorubra IFO 12973 | 38 | −6.52 |

(note)*
Determination of the yield was based on the added (R,S)-3-chloro-1,2-propanediol.

Datum in a literature [Chemistry and Industry, 15, P 533 (1978)] of specific rotatory power of (R)-3-chloro-1,2-propanediol is $[\alpha]_D^{22} -6.9°(c=2, H_2O)$.

After tosylating each sirup in the conventional manner, HPLC analysis (retention time: 35 min. for the (S)-form, and 38.5 min. for the (R)-form was conducted with the chiral column [CHIRALCELL O.C (0.46 cm×25 cm) made by Japan Spectroscopic Co. Ltd.] by employing a mixed solvent (n-hexane : isopropyl alcohol 95:5 (v/v)) at a flow rate of 2.0 ml/min and a wave length of 235 nm. The analysis confirmed that each syrup contained the corresponding (R)-form.

EXAMPLE 4

Serratia marcescens IFO 12648 was inoculated into the culture medium emlpoyed in Examples 1 to 3 and the shaking culture was conducted at 30° C. for 48 hours. The cells were collected by the centrifugation of 50 ml of the culture solution and were washed with water. To a suspension of the cells in 50 ml of 0.3M phosphate buffer (pH 7.0) were added 1 g of (R,S)-3-chloro-1,2-propanediol and each 0.15 g of the compounds having SH group shown in Table 3 to conduct the reaction at 30° C. for 24 hours with shaking.

One milliliter of the reaction mixture was subjected to the extraction with 2 ml of ethyl acetate and the extract was analyzed with a gas chromatography to examine the decomposition rate of the substrate.

Column length: 50 cm

Filler: FAL-M 6%
   support: TENAX GC (made by SHIMADZU CORPORATION)

Carrier gas: $N_2$(22.5 ml/min.)

Column temperature: 175° C.

Detection: FID

Retention time: 1.8 min. (3-chloro-1,2-propanediol)

Table 3 shows an effect of various compounds having SH group on the decomposition rate of the substrate.

TABLE 3

| Compound having SH group | Decomposition rate of the substrate (after 24 hours) (%) | Degree of the effect* |
|---|---|---|
| (Control) | 18 | — |
| Dithiothreitol | 33 | 1.83 |
| Dithioerythritol | 34 | 1.89 |
| Glutathione | 33 | 1.83 |
| Cysteine | 32 | 1.78 |
| Mercaptoethanol | 30 | 1.67 |
| Thioglycerol | 49 | 2.72 |
| 2,3-Dimercaptopropanol | 35 | 1.94 |
| Thioacetic acid | 41 | 2.28 |
| Dimercaptosuccinic acid | 38 | 2.11 |
| 2-Mercaptopropionic acid | 35 | 1.94 |
| 3-Mercaptopropionic acid | 35 | 1.94 |
| Thioglycollic acid | 37 | 2.6 |
| tert-Butyl mercaptan | 29 | 1.61 |
| Sodium hydrosulfide | 40 | 2.22 |
| Potassium hydrosulfide | 42 | 2.33 |

(Note)*

$$\text{Degree of the effect} = \frac{\text{Decomposition rate when the compound is added (after 24 hours)}}{\text{Decomposition rate in control (after 24 hours)}}$$

In the case of the addition of thioglycerol, which showed especially high effect, the purification was conducted in the following manner.

After removing the cells from the reaction mixture by centrifugation, the supernatant was concentrated to about 10 ml and was extracted three times with 20 ml of ethyl acetate (total 60 ml). The extract was dehydrated with anhydrous sodium sulfate and then the solvent was removed under reduced pressure to give a syrup. After distillation of the syrup, specific rotatory power was measured to give the following values.

Addition of thioglycerol:

$[\alpha]_D^{20} = -6.84°(c=2.0, H_2O)$

The above results show that the addition of the compound having SH group does not affect the discrimination of the optical activity, and that (R)-3-chloro-1,2-propanediol can be obtained in the same manner as in the case of control.

In addition to the ingredients used in the Examples, other ingredients can be used in the Examples as set forth in the specification to obtain substantially the same result.

What we claim is:

1. A process for preparing optically active (R)-3-chloro-1,2-propanediol, which comprises subjecting (R,S)-3-chloro-1,2-propanediol to the action of *Serratia marcescens* IFO 12648, IFO 3759, IFO 3736, IFO 3735, IFO 3052 or IFO 3046, *Serratia liquefaciens* IFO 12979 or *Serratia marinorubra* IFO 12973 in a reaction mixture containing dithiothreitol, dithioerythritol, glutathione, cysteine, mercaptoethanol, thioglycerol, 2,3-dimercaptopropanol, thioacetic acid, dimercaptosuccinic acid, 2-mercaptopropionic acid, 3-mercaptopropionic acid, thioglycollic acid, tert-butylmercaptan, sodium hydrosulfide or potassium hydrosulfide, and then separating (R)-3-chloro-1,2-propanediol from the reaction mixture.

* * * * *